United States Patent [19]
Jeretin

[11] 4,112,938
[45] Sep. 12, 1978

[54] DEVICE FOR CONTROLLING THE RESPIRATION IN RESPIRATORS

[75] Inventor: Stojan Jeretin, Ljubljana, Yugoslavia

[73] Assignee: Dragerwerk Aktiengesellschaft, Germany

[21] Appl. No.: 661,275

[22] Filed: Feb. 25, 1976

[30] Foreign Application Priority Data

Feb. 25, 1975 [DE] Fed. Rep. of Germany ....... 2507981

[51] Int. Cl.² .......................................... A61M 16/00
[52] U.S. Cl. ............................... 128/142 R; 128/202; 128/145.5; 128/DIG. 17
[58] Field of Search ............ 128/142 R, 142 G, 142.2, 128/142.3, 145.5, 145.6, 145.7, 145.8, 202, 203, 188, DIG. 17, 2.07, 2.08

[56] References Cited
U.S. PATENT DOCUMENTS

| 2,428,451 | 10/1947 | Emerson | 128/145.7 |
| 4,016,876 | 4/1977 | Martin et al. | 128/202 |

FOREIGN PATENT DOCUMENTS 459,242  4/1975  U.S.S.R. ............................... 128/142 R

OTHER PUBLICATIONS

Mitamura, An Optimally Controlled Respirator, 9/5/71, Bio-Medical Engineering, vol. BME-18, No. 5, pp. 330–337.

Primary Examiner—Robert W. Michell
Assistant Examiner—Henry J. Recla
Attorney, Agent, or Firm—McGlew and Tuttle

[57] ABSTRACT

A device for controlling the respiration to a patient from a respirator in accordance with the partial pressure of the carbon dioxide in the arterial blood or tissue measured in the alveolar expiration air comprises a connection from the patient and the respirator which includes a housing portion with a dead space cavity through which the respiration air must pass. The housing has a partition wall which bounds a part of it and it is connected to a drive motor for moving the partition wall outwardly and inwardly in order to enlarge or reduce the size of the cavity. This outward and inward movement is controlled by a control which is actuated by a sensor which senses the partial $CO_2$ pressure in the respiration gas and regulates the partition wall so as to vary the partial pressure of the $CO_2$ without changing the chosen minute volume of respiration and the pressure.

3 Claims, 1 Drawing Figure

U.S. Patent  Sept. 12, 1978  4,112,938
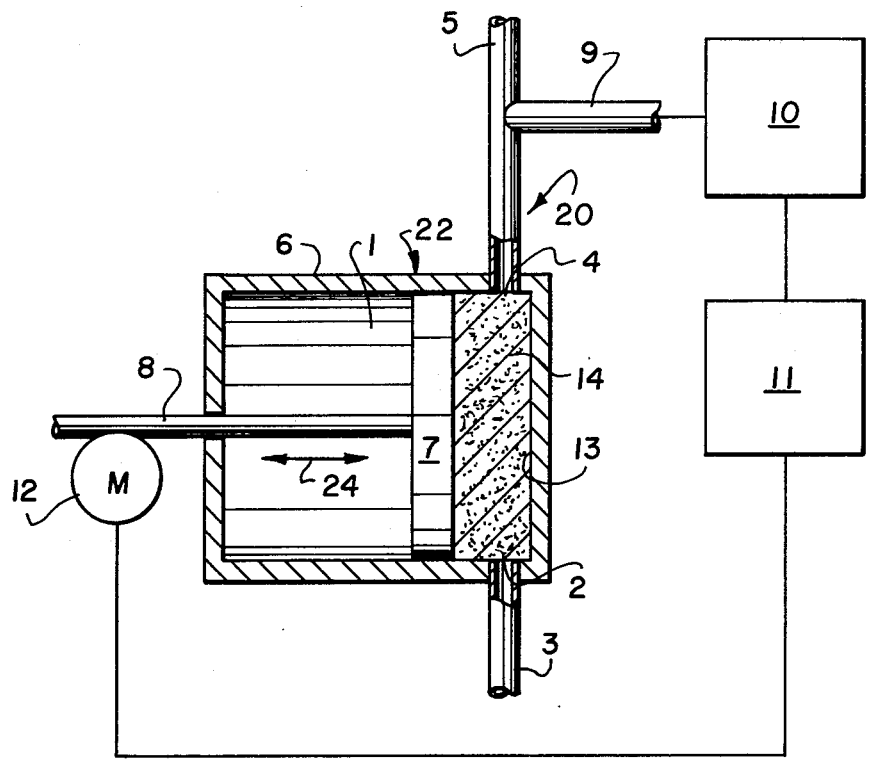

DEVICE FOR CONTROLLING THE RESPIRATION IN RESPIRATORS

BACKGROUND OF THE INVENTION

1. Field of the Invention

This invention relates in general to the construction of respirating devices and in particular to a new and useful device for regulating the operation of the respirator in accordance with a function of the partial pressure of the carbon dioxide in the arterial blood or the tissue through the alveolar expiration air.

2. Description of the Prior Art

The present invention particularly deals with a device for controlling the respiration in respirators as a function of the partial pressure of $CO_2$ in the arterial blood or the tissue through the alveolar expiration air. Up to the present time the mechanism of the respiration control for regulating the respirating air in accordance with its partial pressure of $CO_2$ is not known completely. It is certain however that in respiration the partial pressures of $CO_2$ and oxygen are of substantial importance. In this connection a control of the ventilation on the basis of the arterial $CO_2$ content has proved more appropriate than on the basis of the oxygen concentration.

With a supply of air which is too small the partial pressure of $CO_2$ that is the $P_{CO_2}$ value in the patient's blood increases. This value is balanced with the $CO_2$ content in the alveolar respiration air. A too large amount of inspiration air results in a low partial pressure of $CO_2$. Known respirators determine the partial pressure or content in the expiration air and control the respiration gas regime of the patient in accordance with a predetermined standard. A known respirator comprises a pressure control device with which, by means of a signal from the $CO_2$ meter, the pressure of the inspiration air supplied to the patient is either increased or decreased. With an inspiration air volume which is too small and a correspondingly high $CO_2$ level in the blood, a pressure increase causes a deeper and stronger inspiration. Due to the appropriately induced expiration the partial pressure of carbon dioxide in the blood is reduced. This process continues up to the optimum relation between the volume of the inspiration air and the $CO_2$ level in the blood. Inversely, the pressure in the inspiration air is reduced if the volume is larger than the optimum. With a less deep respiration, the $CO_2$ level will increase. Thus in this respirator the $CO_2$ content is controlled by a pressure variation, with a larger or smaller volume of respiration air resulting therefrom. The apparatus needed for such a purpose is complicated and must be firmly integrated. Such a respirator can be used only for patients in good health having a normal perfusion-to-ventilation ratio. If this ratio is disturbed, for example, in the presence of an embolism, low expiration $CO_2$ values are obtained which in the respirator described would lead to a reduction of the respiratory volume. Such a reduced respiratory volume is incapable of washing out the $CO_2$ produced and this leads to a respiratory acidosis within a short period of time.

Another known respirator controls the oxygen supply through the $CO_2$ content of the expiration air in accordance with the patient's needs. Here again the output of the carbon dioxide meter is compared with a reference value. A differential signal thus produced actuates a tapping valve to change the oxygen content in the inspiration air and the depth of the respiration is remedied. The oxygen supply is controlled within the limits predetermined for the $CO_2$ concentration. The control device comprises a feedback system largely employing electronic component parts. From the physiological point of view, the control of the volume of respiratory air by an oxygen supply is disputed. The electronic equipment of the control system is extensive and its maintenance is not simple.

SUMMARY OF THE INVENTION

The invention provides a device for controlling the respiration in respirators as a function of the $P_{CO_2}$ in the arterial blood or the tissue and in which the predetermined minute volume of the respiration and the pressure remain constant. The device is simple in construction and it is adaptable for use with existing respirator devices without major expenses.

In accordance with the invention a device for controlling the respiration to a patient from a respirator which operates in accordance with the partial pressure of the $CO_2$ in the arterial blood or tissue measured in the alveolar expiration air comprises a connection from the patient to the respirator which includes a housing having a dead space cavity therein through which the respiration air must pass. The housing includes a partition wall which bounds a part of the cavity and which is driven by a drive device in one direction to enlarge the cavity and in another direction to make it smaller. The movement is controlled by a control device which includes means for sensing the partial pressure of the carbon dioxide in the arterial blood or tissue. By varying the size of the cavity the $P_{CO_2}$ value may be controlled to within defined limits without changing the chosen minute volume of respiration or the pressure.

The invention provides the advantage that it is possible to use a larger respiratory volumina during the artificial respiration and thereby prevent or remedy disturbances of the ventilation to blood supply ratio. Any fear of washing out of the $CO_2$ is avoided because a too low arterial $CO_2$ content resulting from the hyperventilation is brought to a standard value by increasing the $CO_2$ content in the inspiration air. The control of this process is based on the continuous measuring of the partial pressure of the $CO_2$. The partial pressure of $CO_2$ which is lower than the desired value records a movement of the cavity wall to cause an enlargement of the cavity so that the $CO_2$ content in the inspiration air will increase. This is because a larger part of the expiration air remains behind in the cavity and becomes a component of the inspiration air during the next inspiration. The increase of the alveolar $CO_2$ content leads to an increase in the arterial partial pressure $CO_2$ value. A too low partial pressure $CO_2$ value might be caused by hyperventilation.

In order to insure a complete scavenging of the cavity during the next inspiration the apparatus is advantageously provided with means for producing a turbulent flow through the cavity.

According to a development of the invention the dead space cavity is connected to the respiration line. The volume of the cavity is determined by a movable partition wall and this partition is adjusted by means of control members in accordance with the difference between the alveolar $CO_2$ content and the preset desired value.

The invention is advantageously provided in a connection which includes a housing which may be mounted directly in the respiration line. The device thus comprises a single member having a variable output and the $CO_2$ value can be controlled with this device alone. Such a device is entirely sufficient for the control of the $CO_2$ and it is not necessary to vary the volume or the pressure of the breathing air. In a preferred form the cavity is bounded by a wall which forms a movable piston which is movable in a cylinder under the control of an actuator or adjusting motor which is controlled by pulses delivered by a $CO_2$ measuring device and/or a computer.

Accordingly it is an object of the invention to provide an improved device for controlling the respiration to a patient from a respirator which includes means for sensing the partial pressure of the $CO_2$ in the respirated gas stream and a connection member between the respirator and the patient including a housing having a cavity with a wall which may be moved to enlarge or reduce the cavity in order to control the $CO_2$ content in response to a desired value of the $CO_2$ content and the determined value by measurement thereof.

A further object of the invention is to provide a device for controlling the respiration in respect to partial pressure of $CO_2$ value in the arterial blood or in the tissue through the alveolar expiration air which is simple in design, rugged in construction and economical to manufacture.

For an understanding of the principles of the invention reference is made to the following description of a typical embodiment thereof as illustrated in the accompanying drawing.

BRIEF DESCRIPTION OF THE DRAWING

The only FIGURE of the drawing is a schematic representation of a device for controlling the respiration to a patient in accordance with the partial pressure of $CO_2$ in the arterial blood or tissue constructed in accordance with the invention.

GENERAL DESCRIPTION OF THE PREFERRED EMBODIMENT

Referring to the drawings in particular the invention embodied therein comprises a device in the form of a connection generally designated 20 having one end 3 connected to a respirator (not shown) and an opposite end 5 connected to the patient for supplying respiratory air to the patient which is exhaled to the respirator and delivered to the line. In accordance with the invention the device includes a housing generally designated 22 which includes a cylinder portion 6 having a front end connected at respective ends 4 and 2 to the respiratory lines 3 and 5 respectively. This front space defines a dead space cavity 13 which is partially closed by a partition wall 7 forming a piston which is movable in the cylinder 6. The cavity 13 may be filled with a granular material 14 which is arranged so as to produce a turbulent flow during the passage of the inspired air through the cavity from the respirator through the line 3, the connection 2, the cavity 13 through the connection 4 to the line 5.

In accordance with a feature of the invention the rod 8 connected to the piston 7 is moved by a drive member or drive means 12 in the directions of the double arrows 24 in order to either enlarge or reduce the size of the cavity 13. The enlargement or reduction is made in accordance with $p_{CO_2}$ value in the arterial blood or the tissue through the alveolar expiration air and such a measurement is made by sensor means arranged in a tap outlet 9 at the respiration line portion 5. Through the tap line 9 a gas sample is taken advantageously at the end of the expiration phase of respiration of the patient. The $CO_2$ content of that alveolar respiration air is largely balanced with the arterial $p_{CO_2}$ value. The sensor means includes a meter 10 for detecting the partial pressure of the $CO_2$ and this is continuously measured and compared with a predetermined desired value which is set in a computer 11 which is connected thereto. When there is a difference between the actual value and the desired values the computer 11 issues a pulse control to the drive means 12 to cause the drive means to either advance or retract the rod 8. A certain value of the expiration air with the alveolar content corresponding to the volume of the cavity 13 is retained in the cavity. This is again supplied to the patient during the next inspiration. In accordance with the determination of the $p_{CO_2}$ value by the measuring instrument 10 the $CO_2$ content in the inspiration air leads to an equilibration with the arterial $p_{CO_2}$ value and, consequently, is directed to produce a difference of zero or the desired $p_{CO_2}$ value.

The flow through the cavity from the line 3 to the line 5 is advantageously controlled so as to produce a desired turbulent flow either by the granular material 14 in the cavity or other well known means.

While a specific embodiment of the invention has been shown and described in detail to illustrate the application of the principles of the invention, it will be understood that the invention may be embodied otherwise without departing from such principles.

What is claimed is:

1. A device for controlling the respiration through a person from a respirator in accordance with the partial pressure of $CO_2$ in the arterial blood or tissue measured in the alveolar expiration air, comprising a housing defining a chamber, a piston movably mounted in said housing for movement in one direction to expand the size of said chamber and in an opposite direction to reduce the size of said chamber, motor means connected to said piston to shift said piston to vary the size of said chamber, a first connection line adapted to be connected to said respirator and connected into said chamber from one side of said housing, a second connection line connected into said chamber from the opposite side of said housing and adapted to be connected to said respirator, sensor control means connected to said second connection line for sensing the partial $CO_2$ pressure therein and connected to said motor to drive said motor to move said piston to vary the size of said chamber thereby, varying the partial pressure of $CO_2$ without changing the chosen minute volume of respiration and pressure.

2. A device according to claim 1, including means associated with said chamber for producing a turbulent flow of respiratory air therethrough.

3. A device according to claim 1, wherein said sensor control means comprises a meter for sensing the $CO_2$ content and a computer connected to said meter and to said drive means and being responsive to a change in the alveolar $CO_2$ content sensed by said meter in respect to a desired value to move said drive means.

* * * * *